US00PP28145P2

(12) United States Plant Patent
Hansen

(10) Patent No.: US PP28,145 P2
(45) Date of Patent: Jun. 27, 2017

(54) ***SCHIZACHYRIUM* PLANT NAMED 'BLUE PARADISE'**

(50) Latin Name: *Schizachyrium scoparium*
Varietal Denomination: Blue Paradise

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/999,481

(22) Filed: May 12, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

A new and distinct cultivar of little bluestem plant, *Schizachyrium scoparium* 'Blue Paradise' has a dense, upright habit. Early foliage coloration becomes nearly a silvery blue that develops into deep wine coloration by fall. The flowers remain effective with reddish-purple tinting into winter and the stems are strongly resistant to lodging.

1 Drawing Sheet

Latin botanical classification: *Schizachyrium scoparium.*
Varietal denomination: 'Blue Paradise'.

BACKGROUND OF THE INVENTION

The present invention relates to a new and distinct cultivar of *Schizachyrium scoparium* and will be referred to hereafter by its cultivar name, 'Blue Paradise' and "the new plant." 'Blue Paradise' represents a new cultivar of little bluestem, an ornamental grass grown for landscape use. The new plant was a single seedling selected at a wholesale perennial nursery in Zeeland, Mich. from the set of open pollinated seed of a proprietary unreleased and unpatented selection named H10-06 as the female or seed parent and an unknown male or pollen parent. Seeds were collected and harvested on Nov. 4, 2011. Following initial evaluations in 2012 and subsequent seasons at the same nursery in Zeeland, Mich. the single selected seedling was assigned the breeder code number H11-07-51.

*Schizachyrium scoparium* 'Blue Paradise' has been successfully propagated by culm division at the same nursery in Zeeland, Mich. since the spring of 2013 and also by sterile plant tissue culture shoot division. The result asexually propagated plants have remained stable and true to type for all traits of the original plant in successive generations.

No plants of *Schizachyrium scoparium* 'Blue Paradise' have been sold in this country or anywhere in the world prior to the filing of this application, nor has any disclosure of the new plant been made prior to the filing of this application with the exception of that which was disclosed within one-year period of the filing of this application and was either derived directly or indirectly from the inventor.

BRIEF SUMMARY OF THE INVENTION AND COMPARISON

The following traits have been repeatedly observed and represent the characteristics of the new cultivar which in combination distinguish *Schizachyrium scoparium* 'Blue Paradise' from all other little bluestem plants known to the inventor:

1. Early foliage coloration of nearly a silvery-blue in summer.
2. Early fall foliage develops deep wine coloration.
3. Upright habit of foliage and stems maintained all season.

*Schizachyrium scoparium* 'Blue Paradise' compares most closely with the little bluestem cultivars 'MinnBlueA' U.S. Plant Pat. No. 17,310 and 'Prairie Blues' (not patented). The female parent H10-06 was less upright and less wine colored in the tall. The male parent of the new plant is unknown, so no comparisons are possible.

Compared to 'Carousel' U.S. Plant Pat. No. 20,948 the new plant has denser foliage, is taller and develops deeper wine colored foliation. Compared to 'Standing Ovation' U.S. Plant Pat. No. 25,202 the new plant is taller and has deeper wine colored foliage in the fall. Compared to 'Blaze' (not patented) the new plant is taller and deeper wine red in the fall. 'Prairie Munchkin' U.S. Plant Pat. No. 26,335 is much shorter and develops more orange in the foliage in fall than the new plant.

The comparison below in Table 1 shows a more succinct differentiation between other known little bluestem cultivars.

TABLE 1

| *Schizachyrium* Cultivars | Height | Fall Foliage Color | Habit |
|---|---|---|---|
| 'Blaze' | 90 cm | orangish-red | upright compact |
| 'Blue Paradise | 100 cm | deep wine-red | upright |
| 'Carousel' | 75 cm | mahogany | upright compact |
| 'MinnblueA' | 120 cm | burgundy tipped blue | upright tall |
| 'Prairie Munchkin' | 75 cm | maroon with orange | tight compact column |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color. The plants in the photographs are of a three-year-old plant grown in a full-sun trial garden in Zeeland, Mich., USA with supplemental water and minimal fertilizer when needed.

DETAILED BOTANICAL DESCRIPTION

Figure 1:
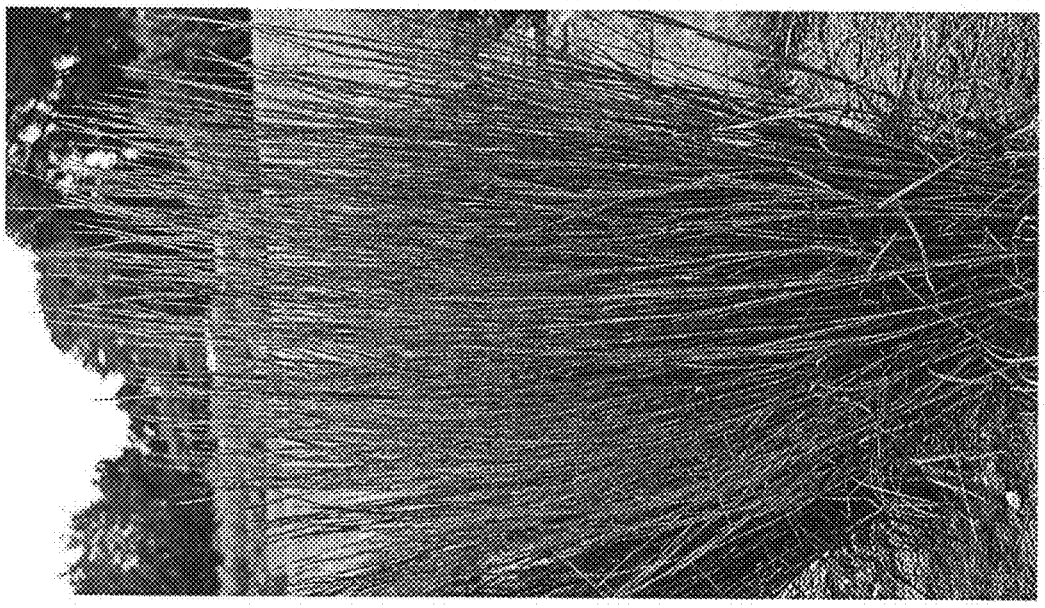
FIG. 1 shows the upright plant habit and mid-summer foliage coloration.
Figure 2:
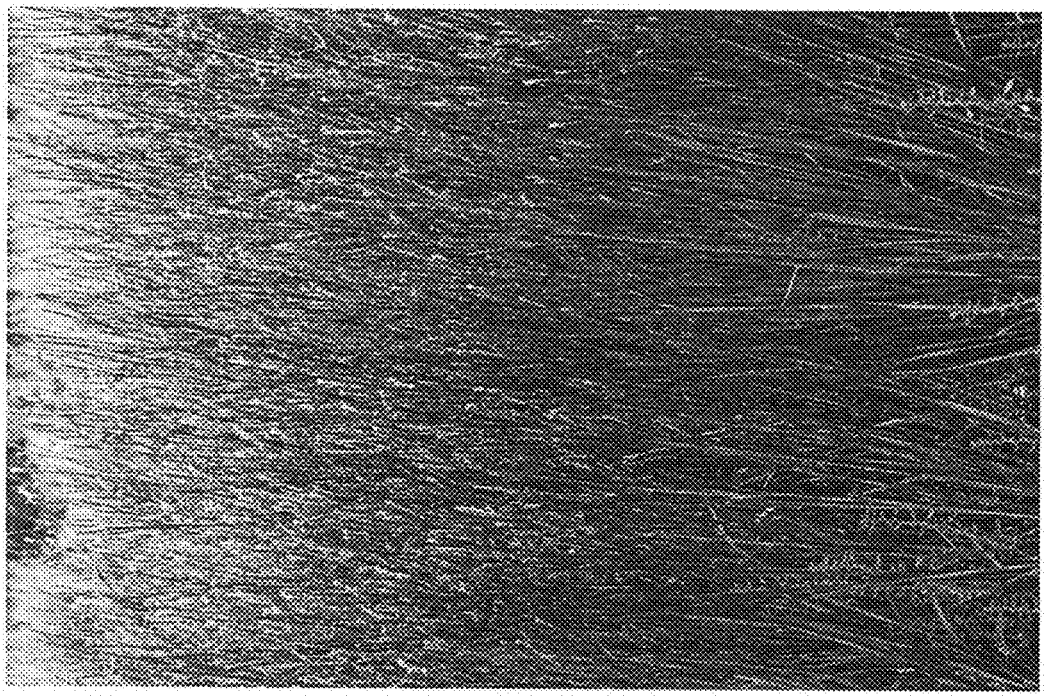
FIG. 2 shows the seed heads and foliage in the fall with deep wine red coloration.

The following detailed description of *Schizachyrium scoparium* 'Blue Paradise' are of taken from a three-year-old plant grown in a full-sun trial field with supplemental water and fertilizer in Zeeland, Mich. The color references are in accordance with the 2001 edition of The Royal Horticultural Society Colour Chart except where common color terms of ordinary dictionary reference are used. The phenotype may vary slightly with different environmental conditions, such as temperature, light, fertility, moisture and maturity levels, but without any change in the genotype.

Female parentage: Proprietary unreleased selection assigned breeder code H10-06.

Male parent: Unknown; uncontrolled open pollination.

Growth rate: Rapid, finishing in 65 mm container from a stage 3 tissue culture plant in two and a half to three months; producing roots in tissue culture in three to four weeks.

Rooting habit: Normal, branching; color of roots near white to tan depending on soil type.

Plant habit: Winter-hardy, herbaceous, perennial grass; compact with upright culms and dense upright foliage.

Plant size: About 100.0 cm tall and about 70.0 cm wide.

Root description: Fibrous, wiry, deep rooted up to about 90 cm long.

Culm: Terete; thin, wiry, strong; glaucous, glabrous; with foliage to near distal end; to about 100.0 cm long, average about 97.0 cm long and 2.5 cm near base; about 4.0 to 6.0 cm of culm exposed between leaves.

Culm color: Seasonally variable; summer blend between RHS 138A and RHS 122B; fall from between RHS 183A and RHS 187B and winter drying to between RHS 177D and RHS 164D.

Nodes: Glabrous, glaucous; average about nine per culm; swollen to about 5.0 mm diameter of lower nodes; internode length between about 11.0 cm on lower internodes and about 2.5 in distal internodes, average about 7.0 cm.

Node color: Nearest RHS 187A by mid-summer and into winter.

Foliage: Leaves flat, alternate, linear; margin entire; glabrous, glaucous; apex narrowly acute, base sheathing and usually open with long split extending to near node; sheath portion up to 8.0 cm long on lowest leaves and 3.0 cm on upper leaves; largest leaves about 18.0 cm long and about 5.0 mm wide; upper leaves average about 7.5 cm long and about 2.0 mm across; six to ten leaves per culm.

Foliage color: On adaxial and abaxial summer between RHS 138A and RHS 122B; fall color nearest RHS N187B on adaxial and abaxial; winter color variable between RHS 177B and RHS 164D on abaxial and adaxial.

Venation: Parallel.

Vein color: Same as surrounding tissue of both abaxial and adaxial.

Ligule: Membranous, fringed apex, about 2.0 mm long and width equal to leaf.

Ligule color: Nearest RHS 158B.

Flower description: Branched raceme at distal three to five nodes; flower period late summer in western Michigan; remaining effective into winter; individual flowers open for two to three days.

Rachis: Glaucous, glabrous; up to about 14.0 cm long, and about 0.5 mm diameter; average about 11.0 cm long and 0.5 mm diameter; frequently with two or three rachis per node.

Rachis color: Variable depending on season and light exposure, nearest RHS 165C with less light exposure and between RHS N186C and RHS N187B with more light exposure and later in season.

Spikelets: In pairs adpressed to rachis; one sessile and one pedicellate; pedicellate spikelet sterile and reduced; sessile spikelet fertile, about 16.0 mm long and about 1.0 mm across.

Glumes: Paired; lemma surrounding inner palea; acute apex; adhering to caryopsis; color nearest RHS N186C with undertones of between RHS 152D to RHS146D.

Lemma: Acute apex; about 7.0 mm long and about 1.0 mm wide; color nearest RHS N186C with undertones of between RHS 152D to RHS146D.

Palea: Acute apex; about 6.0 mm long and about 1.0 mm wide; color nearest RHS 152D.

Awn: Long, thin, nearly hair-like, with membranous base; about 8.0 mm long and base of about 0.5 mm wide, apex about 0.1 mm wide; color between RHS 165C and RHS 165B above the translucent membranous base.

Spikelet hairs: About 3.0 mm long and less than 0.1 mm diameter; collective color nearest RHS N155D.

Reproductive:

*Androecium*.—Typically three. Anther: oblong; basifixed, longitudinal; about 3.0 mm long and about 0.5 mm diameter; color nearest RHS 187B. Filament: very fine, about 0.2 mm diameter and about 2.0 mm long; color nearest RHS 155D. Pollen; abundant; color nearest 187B.

*Gynoecium*.—One. Style: two, plumose, about 2.5 mm long and about 1.0 mm diameter; color nearest RHS 155D. Stigmas: numerous, non-secund, surrounding style; color nearest RHS 186C.

Seed: Caryopsis; enclosed in glume; ovoid with broadly acute apex; less than 1.0 mm long and 0.7 mm diameter; color varies with maturity between RHS 200C and RHS N199D.

Pest and disease resistance: Generally free of pests and diseases, susceptibility or resistance beyond that typical of little bluestem has not been observed; 'Blue Paradise' is highly resistant to lodging; able to withstand adverse weather and still remain upright.

Hardiness: Hard from U.S.D.A. zones 3 to 9; like most little bluestem the new plant is able to withstand some drought once established.

I claim:

1. A new and distinct ornamental cultivar of little bluestem plant, *Schizachyrium scoparium* 'Blue Paradise', as herein described and illustrated, for landscaping the garden en masse or individually.

* * * * *